United States Patent [19]

Rodriguez

[11] Patent Number: 5,115,140

[45] Date of Patent: May 19, 1992

[54] EMR/RFR/MWR BODY SHIELD COMPOSITION

[75] Inventor: Tomas M. Rodriguez, Miami, Fla.

[73] Assignee: Progressive Products, Inc., Miami, Fla.

[21] Appl. No.: 645,425

[22] Filed: Jan. 24, 1991

[51] Int. Cl.⁵ .............................................. G21F 3/02
[52] U.S. Cl. ...................................... 250/516.1; 2/2; 174/35 MS
[58] Field of Search .......................... 250/516.1, 519.1; 174/35 MS; 2/2, 48

[56] References Cited

U.S. PATENT DOCUMENTS 3,996,620 12/1976 Maine ............................................ 2/2
4,678,716 7/1987 Tzeng ............................. 174/35 MS

FOREIGN PATENT DOCUMENTS 8700342 1/1987 World Int. Prop. O. ........ 250/516.1

Primary Examiner—Jack I. Berman

[57] ABSTRACT

EMR/RFR/MWR (Electromagnetic Interference/Radio Frequency Interference/Microwaves) body shield composition comprises a copper base having a coating applied thereon by electroless deposition which may be applied directly to a fabric or other substrate which is inserted into wearing apparel. Preparation of the copper-based coating is also disclosed.

10 Claims, 3 Drawing Sheets

EMR/RFR/MWR BODY SHIELD COMPOSITION

FIELD OF THE INVENTION

This invention relates to a garment protective against electromagnetic radiation (EMR) radio frequency radiation (RFR) and microwave radiation (MWR) emissions from electronic equipment, as well as to coating compositions used to render such garments protective against EMR and/or RFR, and/or MWR. Protection can be afforded to pregnant operators of computers, visual display terminals and microwave ovens. The garment of the invention does not protect against X-ray radiation.

BACKGROUND OF THE INVENTION

Studies indicate that a significantly elevated risk of miscarriage and birth defects exists for pregnant women using these radiation generating devices for more than twenty hours per week.

The present invention is an improvement in shielded aprons of the type shown in U.S. Pat. No. 3,996,620 (Maine, Dec. 14, 1976) which provides inserts of multiple layers of heavy lead sheeting primarily for X-ray radiation protection. Other similar wearing apparel containing heavy lead as the protection against radiation (primarily X-ray) are shown in U.S. Pat. No. 4,196,355 (Maine, Apr. 1, 1980) and U.S. Pat. No. 4,441,025 (McCoy, Jr., Apr. 3, 1984). Heavy lead, however, provides little or no protection against EMR/RFR/MWR emissions. The present invention protection material is a copper-based coating, very lightweight and flexible and designed specifically for protection against EMR/RFR/MWR emission from electronic equipment.

The present invention which also directed to the application of the copper-based coating to fabric or a fabric insert involves the electroless deposition of conductive metal (copper-based) onto virtually any type of substrate. The deposition process, although different, is similar to those processes disclosed and claimed in U.S. Pat. No. 3,904,792 (Gulla et al., Sep. 9, 1975) U.S. Pat. No. 4,568,570 (Giesecke, Feb. 4, 1986), U.S. Pat. No. 4,556,587 (Tsiamis et al., Dec. 3, 1985), and U.S. Pat. No. 4,035,500 (Dafter, Jr., Jul. 12, 1977), all of which are incorporated herein by reference.

SUMMARY OF THE INVENTION

One aspect of the present invention relates to wearing apparel for shielding a wearer from electromagnetic or radio frequency of microwave radiation produced by electronic equipment, wherein the apparel comprises a shell of flexible material containing a flexible insert having a copper-based coating applied thereon sufficient to shield the wearer from the electromagnetic or radio frequency or microwave radiation.

Another aspect of the present invention is a method for making a copper-based coating composition effective as a shield from electromagnetic or radio frequency or microwave radiation produced by electronic equipment comprising the following steps:

(a) preparing electroless plated copper, which comprises the following steps in the order named:
(i) adding to an alcohol reaction bath copper particles to a concentration of about 25.00% to about 35.00% w/v relative to the alcohol component;
(ii) adding distilled water in an amount of about 200.00% to about 300.00% w/v relative to the alcohol component;
(iii) adding a non-ionic surfactant to a concentration of about 0.009% to 0.06% w/v relative to the alcohol component;
(iv) adding a dilute acid to a concentration of about 0.5% to about 2.0% w/v relative to the alcohol component;
(v) adding an anionic surfactant to a concentration of about 0.050% to about 0.100% w/v relative to the alcohol component;
(vi) adding a plating metal to a concentration of about 1.0% to about 4.5% w/v relative to the alcohol component to produce plated copper particles;
(vii) collecting the plated copper particles by filtration;
(viii) washing the treated copper particles with water;
(ix) washing the plated copper particles with alcohol;
(x) adding the plated copper particles to a solvent base resin to produce a plated copper/resin mixture having a plated copper particle to resin ratio of about 0.5:1 to about 8:1; and (b) applying the plated copper/resin mixture to a substrate.

DETAILED DESCRIPTION OF THE PREFERRED EMBODIMENTS

Figure 1:
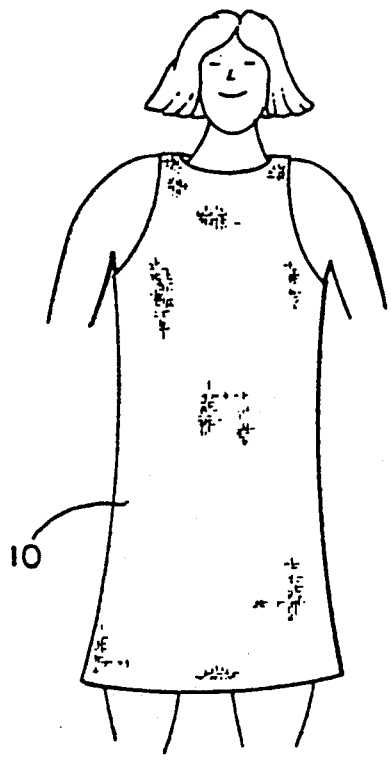
FIG. 1 is a front view of one embodiment of a garment of the present invention as worn by a person.
Figure 2:
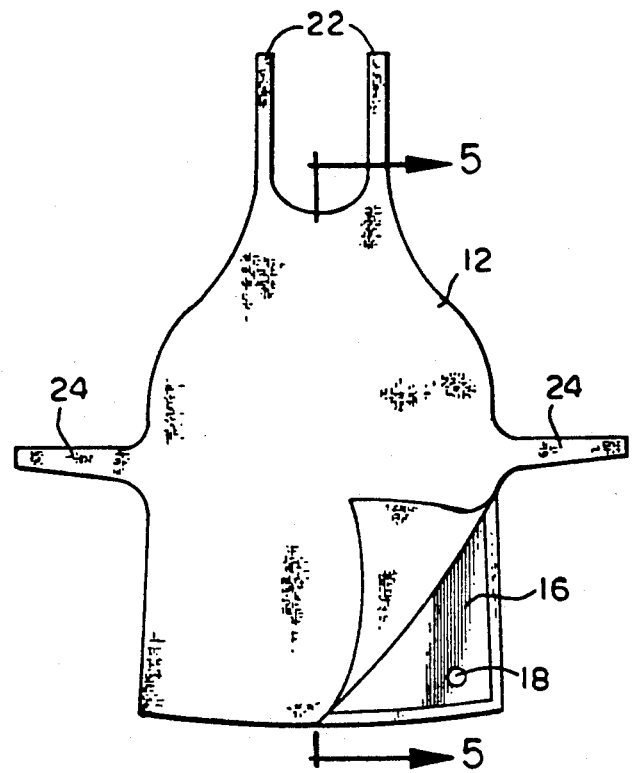
FIG. 2 is a front view of the garment of FIG. 1 with a corner of one layer folded back showing the treated insert.
Figure 3:
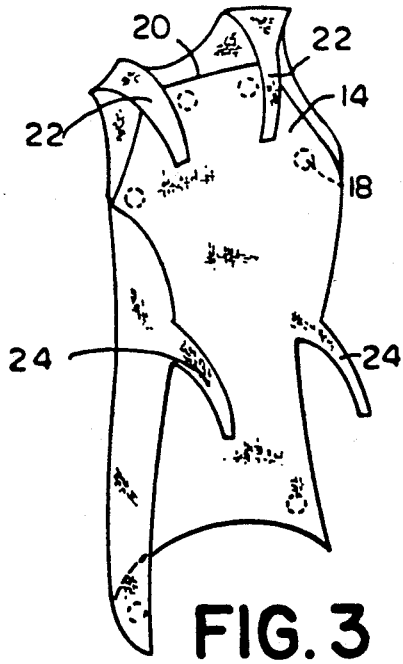
FIG. 3 is a left rear perspective view of the garment of FIG. 2 with both neck ties and waist ties showing.
Figure 4:
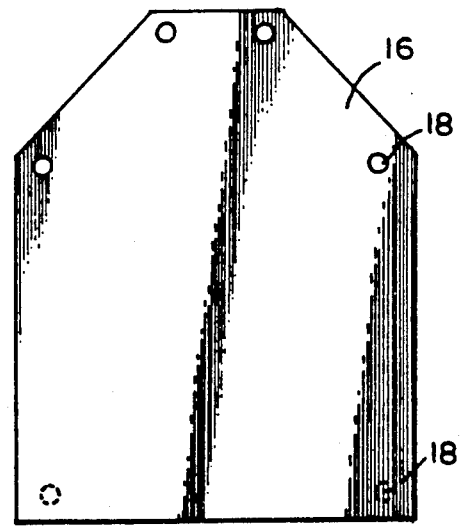
FIG. 4 is a front view of the treated insert used in the garment of FIG. 2.

The invention provides lightweight wearing apparel with a copper-based coating applied on an insert or applied directly on the wearing apparel for protection against EMR/RFR/MWR emissions. The protective wearing apparel is adapted to cove the body from the base of the neck down to below the reproductive organs. The protective wearing apparel of the invention affords maximum protection from EMR/RFR/MWR emissions, thereby reducing the biological effect of such emissions on body organs. The effects, preventable by the protective wearing apparel of the invention, include birth defects, miscarriages, cancer, and other biological effects of EMR/RFR/MWR emissions.

The invention further provides protective wearing apparel which is readily adjustable for maximum shielding protection of wearers of widely varying sizes as well as flexibility. The flexibility of the wearing apparel of the invention results from the use of a lightweight flexible insert in the form of a thermoplastic sheet, such as vinyl, or other lightweight, flexible material. The insert is coated with a non-oxidizing conductive copper-based coating composition prepared by the method of the invention. Other metallic coating materials are well-known in the art and can be applied to the insert in lieu of the coating composition produced by the method of the invention. However, these other metallic coating materials do not afford protection as complete as that afforded by the composition produced in accordance with the present invention. Other shielding coating materials are available from Bee Chemical Company, Lansing, Ill.; Spraylat Corporation, Mount Vernon, N.Y.; Acheson Colloids Company, Port Huron, Mi.; Chomerics Company, Woburn, Mass. and Metachem Resins Corporation, West Warwick, R.I.

The invention further provides for the removal of the insert from the protective wearing apparel enabling the wearer to wash and clean the wearing apparel without impairing the protection provided by the coated insert. The wearing apparel without the insert is made of any type of fabric available in the marketplace. The shielding material can also be applied directly to the fabric without the need for the insert. The invention herein is so light in weight that it does not cause any discomfort and enables complete freedom of movement to the wearer and will easily contour to the body shape of the wearer, whether male or female.

The provisions of the invention are achieved by means of the wearing apparel containing an insert which has applied thereon in a thickness from 0.5 mil to 6 mils, preferably one mil on each side, a non-oxidizing copper conductive coating. The insert sheet coated with the shielding material is inserted into pockets built into the wearing apparel, enabling the shielding protection of the insert to cover the front or the front and back portions of the body, surrounding the torso from the neck down through the reproductive organs.

There are two presently preferred embodiments of the protective wearing apparel of the invention disclosed herein. The first provides protection to the front side of the body only; the second provides protection to the front and back sides of the body.

FIGS. 1 to 5 illustrate wearing apparel 10 of the invention which is protective of the front portion of the body. This embodiment includes a generally rectangular fabric front body panel 12 joined with a fabric back body panel 14 using standard sewing stitching. Into the area between front panel 12 and back panel 14 is placed a coated insert 16.

Figure 5:
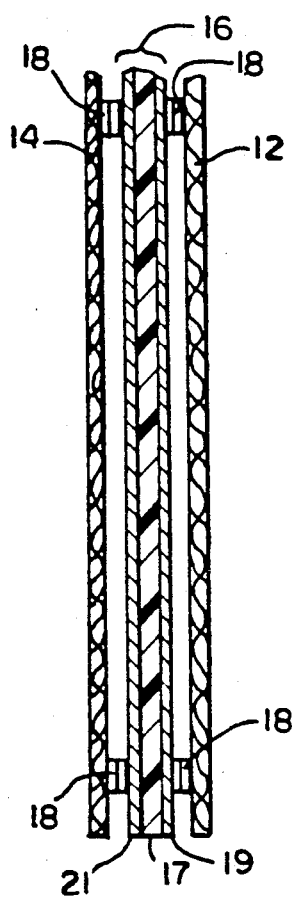
FIG. 5 is an enlarged, cross-sectional view of a portion of the garment taken along line 5—5 of FIG. 2.
Figure 6:
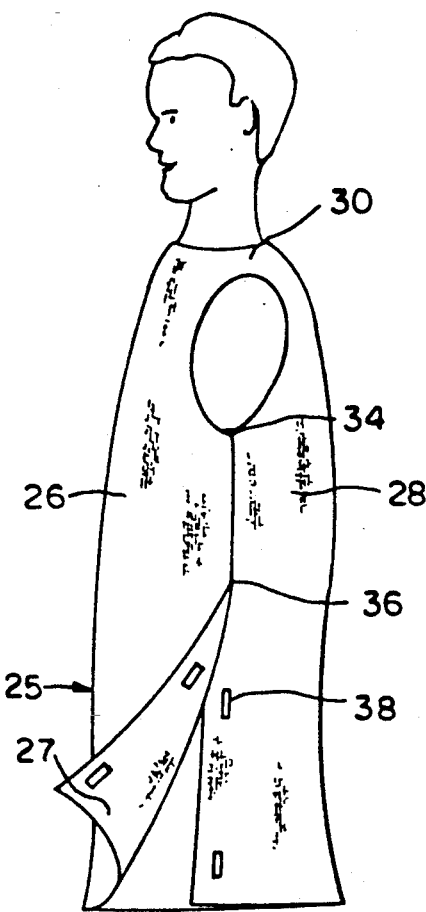
FIG. 6 is a side view of another embodiment of a garment according to the present invention as worn by a person.

As best seen in FIG. 5, the insert 16 comprises an insert body 17 with a front side EMR/RFR/MWR emissions protective metallic coating 19 and a back side EMR/RFR/MWR emissions protective metallic coating 21. The coated insert 16 is attached to the inside of front panel 10 by the use of nonmetallic fasteners 18, thus supporting coated insert 16 so it will contour to the shape of the wearer, whether male or female. Located in back panel 14 is a pocket flap 20 through which coated insert 16 is placed into the wearing apparel. Pocket flap 20 allows easy removal and replacement of coated insert 16 during washing and cleaning procedures for the fabric.

Protective wearing apparel 10 extends downwardly from the top of the shoulders and base of the neck to at least about knee level of the wearer. The protective wearing apparel of the invention must extend from at least under the arm line and downward on the wearer to below the wearer's reproductive organs. Neck ties 22 ar provided to attach to each other to add support to the protective wearing apparel and to hold it in its proper position as shown in FIG. 1. Also included are waist ties 24 attached to opposite sides of apparel 10 at waist level.

In another preferred embodiment of the invention, illustrated in FIGS. 6 to 9, wearing apparel 25 protects both the front and back portions of the wearer's body. The full body protective wearing apparel 25 includes a generally rectangular front body panel having an exterior surface layer 26 and an interior surface layer 27 and a back panel having an exterior surface layer 28 and an interior surface 27. The front panel and back panel are joined together using standard sewing stitching.

Figure 8:
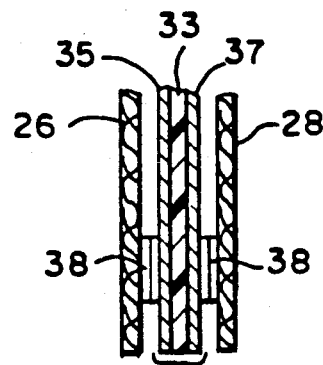
FIG. 8 is a cross-sectional view of the garment taken along line 8—8 of FIG. 7.
Figure 7:
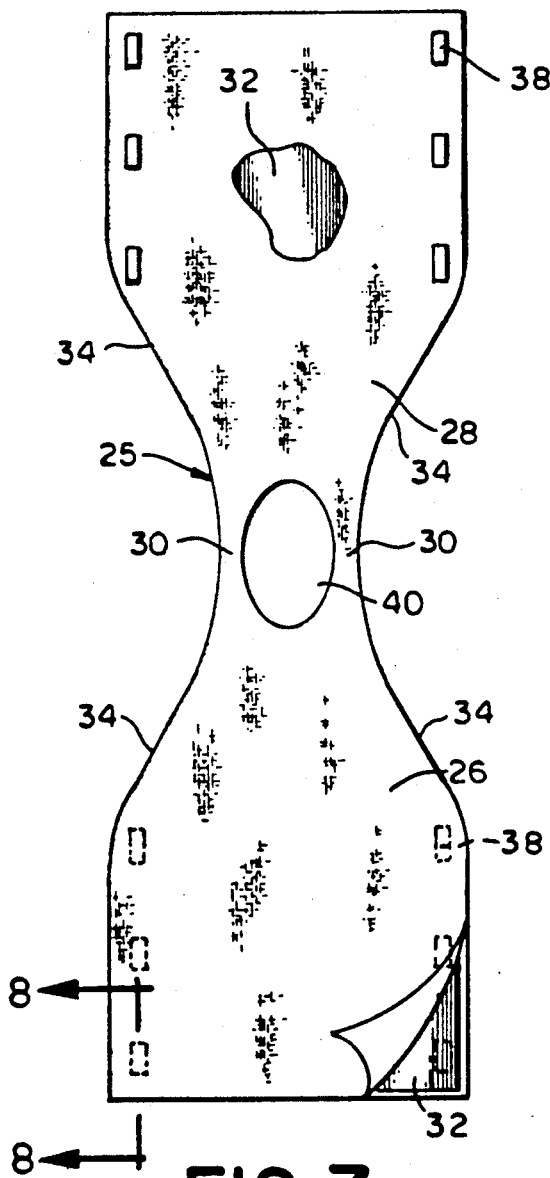
FIG. 7 is a plan view of the front or outer surface of the garment of FIG. 6 including a cutaway and a corner folded back showing the treated insert.
Figure 9:
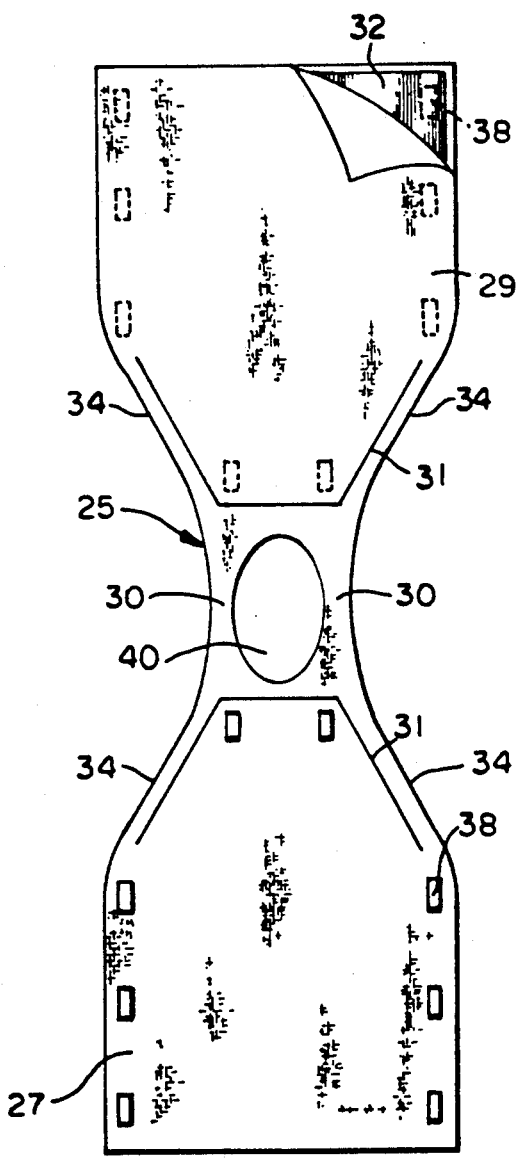
FIG. 9 is a plan view of the back or inside surface of the garment of FIG. 6 including a corner folded back showing the treated insert.

An insert 32 comprises an insert body 33 coated on the front side with a front side EMR/RFR/MWR emissions protective metallic coating 35 and on the back side coated with a back side EMR/RFR/MWR emissions protective metallic coating 37, as best illustrated in FIG. 8. Insert 32 is placed in the front panel and back panel as in the above-described embodiment, the front panel and back panel extend downwardly from the top of the shoulders and base of the neck of the wearer to below the wearer's reproductive organs, preferably through pockets 31 formed in the front and back panels. The protective wearing apparel must, from side to side, extend at least to the arm lines 34, with the front panel creating an overlap 36 with the back panel by at least one inch. Overlap 36 extends from the armpit to the knee area of the wearer. Overlap 36 is maintained by the use of nonmetallic fasteners 38 on interior surface 27 of the front panel and the exterior surface 29 of the rear panel. Two neck straps 30 on opposite sides of a head hole 40 support and position the apparel properly when the apparel is placed over the wearer's head.

The insert of the invention can be coated with many various types of metals, such as copper, which have had a noble metal, e.g., silver, deposited on their surface. To increase the adhesion between the nonmetallic insert of the invention and the metallic coating, dirt, oil and other surface contaminants must be cleaned from the insert using an organic solvent, such as ethanol, methanol, toluene, isopropanol, xylene or methyl ethyl ketone, and preferably ethanol.

After thoroughly mixing the copper-based coating of the method of the invention (discussed below), it can be applied, for example, using a standard air compressor and self-agitation spray gun using an 800 to 1500 needle point and 4 to 8 inches fan spray nozzle set at a hose pressure of 30 to 50 psi. The coating is sprayed on the insert from a distance of 8 to 18 inches from the surface of the nonmetallic insert. It is preferred that a cross hatch pattern be utilized when spraying the copper-based coating onto the insert. The copper-based coating can also be applied to the insert by using any size brush, roller of any material, or by using a dip bath of the coating, for example.

Suitable substrates for the insert of the invention include polyamides, polyethylene fluoride, polyesters, epoxy resins, polyacrylonitrile, polyvinyl halides, polyethylene, polypropylene, acrylonitrile-butadiene-styrene terpolymers, polyalkylene products, such as polycarbonates and other thermoplastic and thermoset synthetic polymers. The thickness of the insert substrates is preferably about 0.05 mil to about 15 mils. and, more preferably, about 4 mils.

If the protective metallic coating is to be applied to other substrates not used as an insert in protective wearing apparel, the substrate to be coated may be of virtually any type. Examples include glass, quartz, ceramics, carbon, paper, polyamides, polyethylene fluoride and textile sheet-like structures, filaments and fibers of polyamide, polyester, polyalkylene, polyacrylonitrile, polyvinyl halides, cotton and wool and mixtures thereof, wood, cement, brick, cinder block, plaster board, or copolymers, graphite fibres, flock and whiskers of aluminum oxide. Textile materials are presently preferred.

A preferred embodiment of the method of the invention relates to the electroless deposition of silver, gold, nickel, tin, platinum, or any combination thereof, or other similar metals, including salt complexes or coordination compounds of these metals onto copper powder comprising flake, shot or other geometric shaped copper. Examples of salt complexes or compounds useful for deposition on copper include silver chloride, gold cyanide and platinum chloride, with silver nitrate being presently preferred. In the method of the invention, it is preferred that copper or other material be pretreated for the uniform non-oxidizing metal coating of the present invention by cleaning or etching using techniques and apparatus known to those skilled in the art. The coated copper or other material exhibits a long-term retention against the environment and provides high electrical conductivity and shielding properties.

The invention will now be described in further detail with reference to the following suitable preparative methods.

Preparation of a Copper-Based Coating

To formulate approximately 1 gallon of the copper-based coating of the present invention, the components used for the electroless deposition of silver on copper were pre-weighed. A container made of polypropylene or polyethylene, or porcelain or glass or any other similar material is preferably used. The container size should be in the range of about 3 gallons to about 5 gallons, the preferred size being about 5 gallons and the container made of polypropylene.

Take a mixer of the ⅛ hp range with attached to it a stainless steel, or polyethylene, or polypropylene mixing blade and rod. Start mixing at 500-900 rpm range but preferably at 700 rpm. Mixing should be continuous throughout the entire procedure.

Add to the container any desired amount of the following water soluble alcohols: isopropanol, butanol, ethanol or methanol. Ethanol is presently preferred. In addition to providing a suitable solvent base for plating copper particles in accordance with the present invention, such water soluble alcohols are believed to aid in the removal of contamination, such as dirt, oil and stearic acid, on the surface of the metal to be plated.

With a mixer rate of about 1000 to 3000 rpm, preferably at a rate of 2200 rpm, add the copper, hereinafter described, very carefully to avoid dusting or any loss of material. Add untreated pure copper flake or shot of any size, and any geometrical shape in an amount of about 15% to about 45% by weight relative to the alcohol and, more preferably, about 30% by weight. One example of copper powder suitable for the copper-based coating composition of the present invention is available from U.S. Bronze, New Jersey, as copper flake powder 3000 C109. Mix for about 20 seconds to about 5 minutes and, more preferably, about 1 minute. At this stage the material in the container consists of the ingredients to be electroless plated with another metal (later described) having better environmental and shielding properties.

Next, to the plated mixture is added distilled water preferably in an amount of about 124% to about 365% and, more preferably, about 250% by weight relative to the alcohol at a temperature of about 90° F. to about 110° F. and, more preferably, about 107° F.

Add to container a water soluble surfactant, such as poly ether modified dimethylpoly siloxane copolymer, sodium tetradecyl oxyethylene, butyl cellosolve or sodium tetradecyl sulfonate in amounts of about 0.009% to 0.06% by weight relative to the alcohol. It is presently preferred to use about 0.003% by weight.

The next step is to dilute the following described ingredient (an acid) with water having a temperature of about 50° F. to about 90° F. in a ratio of about 1:0.5 to about 1:10 with said ingredient. The preferable ratio is about 1:5 and the water temperature is about 70° F. to 75° F. This material is added for the purpose of lowering the pH of the entire batch in the container to pH of about 2 pH to about 8 pH. 4 pH is presently preferred. The ingredient referred to above can be any of the following acids: sulfuric acid, or hydrochloric acid, or nitric acid, or citric acid, or lactic acid preferably in amounts of about 0.6% to about 2.0 and, more preferably, about 1.5% by weight relative to the alcohol. After dilution, add to container and mix for about 10 seconds to about 1.5 minutes, preferably about 30 seconds.

The next anionic surfactant described below is used for the purpose of preparing the site on the copper to be plated so as to enable the copper to accept the plating material more easily. The anionic surfactant acts as a wetting agent. Add to the container amounts of the anionic surfactant of about 0.04% to about 0.10% and, more preferably, about 0.07% by weight relative to the alcohol. Any of the following water soluble anionic surfactants are suitable for the present invention: sodium disulfate, sodium octadecyl sulfate, sodium dioctyl sulfosuccinate and sodium dodecyl sulfate. Mix for 10 seconds to 1.5 minutes and, more preferably, for about 20 seconds.

Increase the speed of mixing to about 3000 to about 6000 rpm, preferably about 3400 rpm. The next ingredient is the metal that is used to plate the copper. Add to the container and mix for 20 seconds to 5 minutes (preferably for 1 minute) the amounts of about 0.6% to about 2.0% and, more preferably, about 1.5% by weight relative to the alcohol of any of the following ingredients: silver acetate, silver cyanide, platinum chloride, silver nitrate, gold cyanide, or silver chloride. However, this is only a partial list and one skilled in the art will appreciate that other noble metals are available. Silver nitrate ($AgNO_3$, FW 169.88) is the presently preferred plating metal.

The next step is a washing procedure as below described to remove all traces of unused ingredients. When preparing relatively large quantities of plated copper particles in accordance with the present invention, the application of centrifugal force is preferred for easier and more efficient and uniform removal of waste products. In addition, quicker removal of the acid added previously will reduce any excess damage to the plated copper. For example, while not wishing to be bound by any particular theory, the inventor believes that failure to remove the acid component of the preparation in a timely fashion may cause oxidation and breakdown of the plating metal. Where washing is expected to take more than about 30 to 90 minutes, it is presently preferred to conduct the wash procedures in a centrifuge apparatus. A centrifuge, such as the Bock Model No. 955 centrifuge available from Bock, Toledo, Ohio is believed to be suitable for use in accordance with the present invention.

For smaller, more easily manipulated preparations, such as those examples disclosed herein, a flask of glass, or porcelain, or polyethylene, or polypropylene or any other similar material with a side hose connection and a Buchner funnel made of glass, or porcelain, or polyethylene, or polypropylene or any other similar material, with a rubber stopper used to mate the flask to the Buchner funnel may be used in the washing procedure. Inside the Buchner funnel place a filter paper to permit the unused fluids to pass through the filter and to retain the plated copper particles. Connect this filtration system (flask and Buchner funnel) to a hose connected to a ¼ hp vacuum pump.

The vacuum pump will draw the air from the flask thereby permitting the liquids described below to flow past the treated copper particles, thus removing the unused ingredients by washing them and leaving a monomolecular layer of the surfactant. To implement the foregoing objective, take the complete plating bath in the container and strain it through the above-described filtration equipment to enable the separation of the plated copper particles from the plating solutions.

Next, wash the copper particles as above-described in water preferably having a temperature of about 70° F. to about 75° F. Preferably, about 0.5 to about 2 liters of water is used for every kilogram of plated copper particles. Wait for the copper particles to dry (about 10 seconds to about 5 minutes). Next, wash the copper particles using an alcohol, such as methanol, isopropanol, ethanol or normal butanol alcohol in an amount sufficient to remove any traces of water. Alcohol washing may be done with the filtration system in the same manner as the water above-described. Preferably, about 0.5 to 2.0 liters of alcohol is used for every kilogram of plated copper particles.

Finally, to remove the alcohol and any remaining water, a stronger solvent is used by flowing through the filtration system in the same manner as above-described. Suitable solvents include methyl ethyl ketone, toluene, acetone and xylene, preferably in the amount of about 0.5 to 2.0 liters per kilogram of plated copper particles.

The operating vacuum pump should continue to run for 30 seconds to 15 minutes (preferably at least 3 to 5 minutes) so air can flow through the treated copper particles to aid the drying process.

To make a coating composition using the electroless plated copper, place the dried, treated copper particles in a stainless steel or any other similarly-made material container and add to the container a resin system in an amount sufficient to create a plated copper:resin mixture ratio of about 0.5:1.0 to about 8:1 and, more preferably, about 4.1:1.0 by weight solids. Suitable resin systems include any thermoplastic acrylic resin, polyurethane resin, epoxy resin, copolymer alkyd resin, acrylic copolymer or virtually any other paint resin system available.

Into the stainless steel container add any of many different available organic solvents, such as toluene, xylene, methyl ethyl ketone, acetone, n-butanol, methanol, methyl isobutyl ketone, or any other commercially available solvent and any possible combination thereof in any amount desired to achieve a desired consistency for application.

One presently preferred composition of the present invention comprises the following ingredients in the amounts set forth in Table 1.

TABLE 1

| Electroless Plating Composition | |
|---|---|
| Compound | Quantity |
| 1. Ethyl alcohol (denatured, 95%) | 2994.33 g |
| 2. Copper powder | 905.99 g |
| 3. Distilled water | 7546.97 g |
| 4. Poly ether modified dimethylpoly siloxane copolymer | 0.089 g |
| 5. Nitric acid, 70% | 45.30 g |
| 6. Sodium dioctyl sulfosuccinate | 2.24 g |
| 7. Silver nitrate | 45.30 g |

Test Results of Copper-Based Coating

The copper-based coating produced in accordance with the present invention was tested by Raytheon Corporation, Equipment Division, Environmental Engineering, Wayland, Massachusetts. The results are indicated in Table 2.

TABLE 2

| Test Results | |
|---|---|
| SYSTEM: | One component acrylic solvent resin based system |
| COLOR: | Metallic copper |
| SOLIDS: | 30% ± 1% by weight |
| SOLVENTS: | Toluene, Xylene |
| VISCOSITY: | 24 sec ± 2 #2 Zahn Cup |
| DENSITY: | 8.41 lbs per gallon |
| DRYING TIME: | 30 min. air dry - complete |
| | 10 min. at 120° F. - complete |
| | 1 hour at room temperature - complete |
| APPLICATION METHOD: | Self-agitation cup gun, brush, roller or dip bath method |
| FILM THICKNESS: | 1 mil |
| | 3 mils |
| CONDUCTIVITY: | .10 OHM/1" sq. (1 mil) |
| | .08 OHM/1" sq. (3 mils) |
| ADHESION: | Excellent to most plastic |
| COHESION: | Excellent |
| HUMIDITY RESISTANCE: | Passes Mil-Spec 810C, two cycles - no effect |
| FLEXIBILITY: | DJT 4000 - good; DJT 4003 (another family product) - excellent |
| ATTENUATION: | 1 mil on one side - average 63 db to 1 GH$_z$ |
| | 3 mils on one side - average 68 db to 1 GH$_z$ |
| | 1 mil on both sides - average 79 db to 1 GH$_z$ |
| | 3 mils on both sides - average 79.5 db to 1 GH$_z$ |
| SHELF LIFE: | 1 Year - recommended per industry standards. Product itself unaffected. Longer shelf life is existent. |
| COVERAGE: | At 3 mils 350 sq. ft./gal. at 100% efficiency. |
| LONGEVITY: | Product itself indefinite - integrity of substrates may affect product, i.e., building settling (5-7 years). Periodic checks to be made. |
| ELASTICITY: | Excellent |
| POROUS SUBSTRATES: | Product not affected. Coverage effect inconsequential |
| APPLICATION: | Air compressor, self-agitation spray gun, well ventilated area, and semi-skilled supervised labor |

To demonstrate the effects of using less of and omitting some of the ingredients in the coating, as heretofore described, the following modifications to the compositions were made as noted in Examples 3-12, with the indicated effects.

Preparation Without Anionic Surfactant (Comparative)

The removal of an anionic surfactant provides an effective coating but not up to the optimum levels of the invention as heretofore specifically described.

TABLE 3

| COMPOSITION | |
|---|---|
| 1. Ethyl alcohol (denatured, 95%) | 2994.33 g |
| 2. Copper powder | 905.99 g |
| 3. Distilled water | 7546.97 g |
| 4. Poly ether modified dimethylpoly siloxane copolymer | 0.089 g |
| 5. Nitric Acid HNO₃ 70% FW 63.01 | 45.30 g |
| 6. Silver Nitrate AgNO₃ | 45.30 g |

The composition set forth in Table 3 revealed a large decrease in EMR/RFR/MWR shielding properties to the point of not being efficient for the standards required under even the mildest of environmental requirements and conditions. This particular combination of ingredients resulted in a very unstable and non-uniform level of plating.

Preparation with Higher Anionic Surfactant Concentration (Comparative)

The anionic surfactant, sodium dioctyl sulfosuccinate, was added in an increased amount of 22.45 grams (0.75%). Except for the foregoing change, the composition was the same as that set forth in Table 1.

The results of the coating in this example were favorable in terms of conductivity and shielding properties. However, the major problem arising was an almost unwashable first stage wash of the copper ingredient. The amount of water needed to remove the extra sodium dioctyl sulfosuccinate was approximately 2.5 gallons.

The results obtained did not warrant the waste of material and time for there was no appreciable increase in properties.

Preparation with Decreased Anionic Surfactant Concentration (Comparative)

A three-fold decrease of sodium dioctyl sulfosuccinate to the levels of 0.75 grams (0.02%) did not produce the same disadvantages as with no surfactant or increased surfactant. However, the optimum traits desired for EMR/RFR/MWR shielding were not achieved. Except for the foregoing alteration, the composition remained the same as set forth in Table 1.

Preparation with Decreased Plating Metal (Comparative)

The ratio between the copper flake and the plating metal is important. An improper balance will either destroy the effectiveness or will cause the end product to be costly to produce in any quantity. A decrease of 50% of silver nitrate from that set forth in Table 1 was used resulting in the composition shown in Table 4.

TABLE 4

| COMPOSITION | |
|---|---|
| 1. Ethyl alcohol (denatured, 95%) | 2994.33 g |
| 2. Copper powder | 905.99 g |
| 3. Distilled water | 7546.96 g |
| 4. Poly ether modified dimethylpoly siloxane copolymer | 0.089 g |

TABLE 4-continued

| COMPOSITION | |
|---|---|
| 5. Nitric acid 70% | 45.30 g |
| 6. Sodium dioctyl sulfosuccinate | 2.24 g |
| 7. Silver nitrate | 22.65 g |

The results obtained were a definite decrease in shielding effectiveness of approximately 25% from the optimum average attenuation of 80 dB protection desired to 59 dB shielding protection.

Preparation with Decreased Plating Metal (Comparative)

A further decrease in the plating metal component of the copper-based composition of the present invention reflected an increased loss of shielding protection. Further reducing silver nitrate by 75% from the composition set forth in Table 1 resulted in a virtually complete loss of shielding protection. Although short-term levels of conductivity may be present, the resulting product will not be environmentally stable.

Preparation with Increased Copper (Comparative)

Increasing the copper amount as shown in the composition below to 3714.00 grams (124%) in lieu or 905.99 grams (30%) resulted in the ratio of silver nitrate and copper being at a level that produced an unbalanced coating with virtually no effective shielding.

A certain level of silver nitrate as shown in the ranges heretofore set forth in the specification is necessary to coat the copper flake surface properly.

TABLE 5

| COMPOSITION | | |
|---|---|---|
| Ingredients | Range | Quantity |
| 1. Ethyl alcohol (denatured, 95%) | 70° F.–75° F. | 2994.33 g |
| 2. Copper powder | | 3,714.56 g |
| 3. Distilled water | | 7546.96 g |
| 4. Poly ether modified dimethylpoly siloxane copolymer | | 0.089 g |
| 5. Nitric Acid HNO₃ 70% FW 63.01 | | 45.30 g |
| 6. Sodium Dioctyl Sulfosuccinate | | 2.24 g |
| 7. Silver Nitrate AgNO₃ FW 169.88 | | 22.65 g |

Preparation with Alternative Solvents (Comparative)

Use of solvents, other than alcohol, in the composition of the formulation as set forth in Table 1, such as toluol, xylol, and just about any other solvent which is not soluble in water, resulted in a total failure of the product. With such alternative solvents, the copper coagulated and formed large lumps with no practical method to reverse and cure this problem.

Preparation with Increased Non-Ionic Surfactant (Comparative)

A fifteen-fold increase of non-ionic surfactant from that set forth in Table 1 neither hastened nor retarded the reaction time of the plating process. Although the properties remain the same, the cost will increase.

Preparation With Decreased Acid (Comparative)

A decrease in the amount of nitric acid to below a level of 5% of the level of copper, as set forth in Table 1, resulted in either too slow a rate of plating and an uneven or non-uniform coverage of the copper flake. Additionally, the pH rises to a very high and unstable level.

Preparation with Increased Acid and Plating Metal (Comparative)

An alteration of the ratio of copper, nitric acid, and silver nitrate set forth in Table 1 by more than 5% based on the copper, reduces the shielding effectiveness.

Even though the results obtained by said alteration may be acceptable to some degree for certain standards and requirements, the maximum shielding advantages of the invention are not achieved.

The present invention may be embodied in other specific forms without departing from the spirit or essential attributes thereof and, accordingly, reference should be made to the appended claims, rather than to the foregoing specification as indicating the scope of the invention.

I claim:

1. Wearing apparel for shielding a wearer from electromagnetic or radio frequency or microwave radiation produced by electronic equipment; wherein the apparel comprises a shell of flexible material containing a flexible insert having a copper-based coating applied thereon in an amount sufficient to shield the wearer from the electromagnetic, radio frequency or microwave radiation; the insert being made by the following steps:
   (a) preparing electroless plated copper, which comprises the following steps in the order named:
      (i) adding to an alcohol reaction bath copper particles to a concentration of about 25% to about 35% w/v relative to the alcohol component;
      (ii) adding distilled water in an amount of about 200.00% to about 300.00% w/v relative to the alcohol component;
      (iii) adding a non-ionic surfactant to a concentration of about 0.0009% to 0.06% w/v relative to the alcohol component;
      (iv) adding a dilute acid to a concentration of about 0.5% to about 2.0% w/v relative to the alcohol component;
      (v) adding an anionic surfactant to a concentration of about 0.050% to about 0.100% w/v relative to the alcohol component;
      (vi) adding a plating metal to a concentration of about 1.0% to about 4.5% w/v relative to the alcohol component to produce plate copper particles;
      (vii) collecting the plated copper particles by filtration;
      (Viii) washing the treated copper with water;
      (ix) washing the plated copper particles with alcohol;
      (x) adding the plated copper particles to a solvent base resin to produce a plated copper/resin mixture having a plated copper particle to resin ratio of about 0.5:1 to about 8:1, and
   (b) applying the plated copper/resin mixture to a substrate.

2. The wearing apparel of claim 1 adapted for shielding a front portion of the wearer's torso.

3. The wearing apparel of claim 1 adapted for shielding the wearer's entire torso.

4. The wearing apparel of claim 1, wherein the shell of flexible material is a fabric material.

5. The Wearing apparel of claim 1, wherein the insert is a plastic sheet.

6. The wearing apparel of claim 5, wherein the plastic sheet is selected from the group consisting of polyamides, polyethylene fluoride, polyesters, epoxy resins, polyacrylonitrile, polyvinyl halides, polyethylene, polypropylene, polycarbonate, acrylonitrile-butadiene-styrene terpolymers, polyalkylene products and other thermoplastic and thermoset synthetic polymers.

7. The wearing apparel of claim 1, further comprising a pocket formed in the flexible shell adapted for containing the insert.

8. The wearing apparel of claim 1, wherein the copper-based coating comprises copper having a plating of a metal selected from the group consisting of silver, gold, platinum, nickel and tin.

9. The wearing apparel of claim 8, wherein the copper-based coating further comprises an acrylic resin and an organic solvent.

10. The wearing apparel of claim 1, further comprising means for attaching the apparel to the wearer's body.

* * * * *